(12) United States Patent
Smith

(10) Patent No.: US 10,908,187 B2
(45) Date of Patent: Feb. 2, 2021

(54) CURRENT SENSOR WITH REDUCED VOLTAGE COUPLING

(71) Applicant: COVIDIEN LP, Mansfield, MA (US)

(72) Inventor: Robert B. Smith, Loveland, CO (US)

(73) Assignee: Covidien LP, Mansfield, MA (US)

(*) Notice: Subject to any disclaimer, the term of this patent is extended or adjusted under 35 U.S.C. 154(b) by 635 days.

(21) Appl. No.: 15/144,341

(22) Filed: May 2, 2016

(65) Prior Publication Data
US 2017/0315155 A1 Nov. 2, 2017

(51) Int. Cl.
*G01R 15/18* (2006.01)
*A61B 18/12* (2006.01)
*A61B 18/00* (2006.01)

(52) U.S. Cl.
CPC ........ *G01R 15/185* (2013.01); *A61B 18/1206* (2013.01); *G01R 15/181* (2013.01); *A61B 2018/00178* (2013.01); *A61B 2018/00827* (2013.01); *A61B 2018/00833* (2013.01); *A61B 2018/1286* (2013.01)

(58) Field of Classification Search
CPC ................ G01R 15/181; G01R 15/185; A61B 18/1206; A61B 2018/00827; A61B 2018/00833; A61B 2018/1286; A61B 2018/1293
See application file for complete search history.

(56) References Cited

U.S. PATENT DOCUMENTS

| 3,252,052 A | 5/1966 | Nash |
| 3,601,126 A | 8/1971 | Estes |
| 3,683,923 A | 8/1972 | Anderson |
| 3,697,808 A | 10/1972 | Lee |
| 3,885,569 A | 5/1975 | Judson |
| 3,913,583 A | 10/1975 | Bross |
| 4,102,341 A | 7/1978 | Ikuno et al. |

(Continued)

FOREIGN PATENT DOCUMENTS

| EP | 0694291 A1 | 1/1996 |
| EP | 2281521 A1 | 2/2011 |

(Continued)

OTHER PUBLICATIONS

Kojovic, L: "PCB Rogowski Coils Benefit Relay Protection", IEEE Computer Applications in Power, IEEE Inc., NY, vol. 15, No. 3, Jul. 1, 2002, pp. 50-53.

(Continued)

*Primary Examiner* — Jaymi E Della
*Assistant Examiner* — Sean W Collins
(74) *Attorney, Agent, or Firm* — Carter, DeLuca & Farrell LLP

(57) ABSTRACT

A current sensor includes a current sense coil disposed about a conductive lead, the current sense coil configured to sense a current passing through the conductive lead. The current sense coil includes: a first outer coil configured to detect a first magnetic field generated by the current; a second outer coil configured to detect the first magnetic field, the second outer coil further configured to cancel an electrical field induced in the first outer coil; and an inner conductor disposed between the first outer coil and the second outer coil, the inner conductor configured to detect a second magnetic field generated by the current.

14 Claims, 9 Drawing Sheets

(56) References Cited

U.S. PATENT DOCUMENTS

| | | |
|---|---|---|
| 4,437,464 A | 3/1984 | Crow |
| 4,569,345 A | 2/1986 | Manes |
| 4,754,757 A | 7/1988 | Feucht |
| 5,067,953 A | 11/1991 | Feucht |
| 5,540,684 A | 7/1996 | Hassler, Jr. |
| 5,817,091 A | 10/1998 | Nardella et al. |
| 5,830,212 A | 11/1998 | Cartmell et al. |
| 6,313,623 B1 | 11/2001 | Kojovic et al. |
| 6,440,157 B1 | 8/2002 | Shigezawa et al. |
| 6,511,478 B1 | 1/2003 | Burnside et al. |
| 6,566,994 B1 * | 5/2003 | Jensen ............... G01R 15/181 336/174 |
| 6,624,624 B1 | 9/2003 | Karrer et al. |
| 6,731,193 B2 | 5/2004 | Meier et al. |
| 6,822,547 B2 | 11/2004 | Saito et al. |
| 6,979,329 B2 | 12/2005 | Burnside et al. |
| 7,041,096 B2 | 5/2006 | Malis et al. |
| 7,106,162 B2 | 9/2006 | Saito |
| 7,736,359 B2 | 6/2010 | McPherson |
| 8,152,800 B2 | 4/2012 | Behnke |
| 8,398,627 B2 | 3/2013 | Hosier |
| 9,116,179 B2 | 8/2015 | Gilbert |
| 2003/0181898 A1 | 9/2003 | Bowers |
| 2004/0178875 A1 | 9/2004 | Saito |
| 2004/0257061 A1 | 12/2004 | George de Buda |
| 2007/0063664 A1 | 3/2007 | Rhodes et al. |
| 2007/0152651 A1 * | 7/2007 | Shiokawa ............ G01R 15/181 324/76.11 |
| 2008/0071260 A1 | 3/2008 | Shores |
| 2008/0079418 A1 | 4/2008 | Rea et al. |
| 2009/0013526 A1 | 1/2009 | Yang et al. |
| 2009/0036883 A1 | 2/2009 | Behnke |
| 2009/0058398 A1 * | 3/2009 | Ibuki .................... G01R 15/181 324/126 |
| 2009/0243590 A1 | 10/2009 | West et al. |
| 2010/0114090 A1 | 5/2010 | Hosier |
| 2013/0023870 A1 | 1/2013 | Collins |
| 2013/0023871 A1 | 1/2013 | Collins |
| 2014/0167733 A1 | 6/2014 | Buck et al. |

FOREIGN PATENT DOCUMENTS

| | | |
|---|---|---|
| EP | 2407116 A1 | 1/2012 |
| EP | 2510895 A1 | 10/2012 |
| EP | 2742887 | 6/2014 |
| WO | 0072027 A1 | 11/2000 |
| WO | 02/00129 | 1/2002 |
| WO | 2010007017 A1 | 1/2010 |

OTHER PUBLICATIONS

Kojovic, L : "PCB Rogowski Coil Designs and Performances for Novel Protection Relaying", Institute of Electrical and Electronics Engineers, vol. 2, Jan. 1, 2003 pp. 609-614.

European Search Report dated Oct. 10, 2017 issued in corresponding EP Application No. 17168928.4.

European Examination Report dated Feb. 12, 2019 issued in corresponding EP Appln. No. 17168928.4.

* cited by examiner

CURRENT SENSOR WITH REDUCED VOLTAGE COUPLING

BACKGROUND

Technical Field

The present disclosure relates to a current sensor for use with an electrosurgical generator configured to generate a radio frequency ("RF") waveform. In particular, the present disclosure relates to a current sense coil configured to eliminate and/or minimize effects of external voltage coupling.

Background of Related Art

Electrosurgery involves application of high radio frequency electrical current to a surgical site to cut, ablate, desiccate, or coagulate tissue. In monopolar electrosurgery, a source or active electrode delivers RF alternating current from the electrosurgical generator to the targeted tissue. A patient return electrode is placed remotely from the active electrode to conduct the current back to the generator.

In bipolar electrosurgery, return and active electrodes are placed in close proximity to each other such that an electrical circuit is formed between the two electrodes (e.g., in the case of an electrosurgical forceps). In this manner, the applied electrical current is limited to the body tissue positioned between the electrodes. Accordingly, bipolar electrosurgery generally involves the use of instruments where it is desired to achieve a focused delivery of electrosurgical energy between two electrodes.

Conventional RF generators utilize a variety of sensors to measure properties of the generated RF waveforms. However, some of the sensors are more susceptible to external voltage coupling, which affects the accuracy and reliability of the measured signals. In particular, current sensors which utilize a sense coil are particularly susceptible to secondary or tertiary order current or voltage sources that are orthogonal to the flow of current being measured. This susceptibility introduces noise into the measured signals, thereby reducing inherent measurement accuracy of the sense coil. Accordingly, this makes measurements of very small currents, such as those generated by RF generators, inaccurate and unreliable. Although there have been attempts to design current sense coils by balancing and/or cancelling external electrical fields and other sources of interference, there is a need for an RF current sense coil configured to reduce and/or eliminate external voltage coupling.

SUMMARY

According to one embodiment of the present disclosure, a current sensor is disclosed. The current sensor includes a current sense coil disposed about a conductive lead, the current sense coil configured to sense a current passing through the conductive lead. The current sense coil includes: a first outer coil configured to detect a first magnetic field generated by the current; a second outer coil configured to detect the first magnetic field, the second outer coil further configured to cancel an electrical field induced in the first outer coil; and an inner conductor disposed between the first outer coil and the second outer coil, the inner conductor configured to detect a second magnetic field generated by the current.

According to another embodiment of the present disclosure, an electrosurgical generator is disclosed. The electrosurgical generator includes: a power supply configured to output a direct current; a power converter coupled to the power supply, the power converter configured to generate a radio frequency current based on the direct current; at least one lead coupling the power converter to a terminal configured to couple to an electrosurgical instrument; and a current sensor. The current sensor includes: a current sense coil disposed about the at least one lead, the current sense coil configured to sense the radio frequency current passing through the at least one lead. The current sense coil includes: a first outer coil configured to detect a first magnetic field generated by the radio frequency current; a second outer coil configured to detect the first magnetic field, the second outer coil further configured to cancel an electrical field induced in the first outer coil; and an inner conductor disposed between the first outer coil and the second outer coil, the inner conductor configured to detect a second magnetic field generated by the radio frequency current.

According to one aspect of any of the above embodiments, each of the first outer coil and the second outer coil includes a first balancing portion and a second balancing potion.

According to one aspect of any of the above embodiments, the first balancing portion of the first outer coil and the second balancing portion of the second outer coil are coupled to a first lead.

According to one aspect of any of the above embodiments, the second balancing portion of the first outer coil and the first balancing portion of the second outer coil are coupled to a second lead.

According to one aspect of any of the above embodiments, the current sensor further includes a conditioning circuit coupled to the first lead and the second lead.

According to one aspect of any of the above embodiments, each of the first outer coil and the second outer coil are coupled to the inner conductor.

According to one aspect of any of the above embodiments, the current sensor further includes a printed circuit board having a plurality of dielectric layers.

According to one aspect of any of the above embodiments, each of the first outer coil, the second outer coil, and the inner conductor are disposed on a corresponding dielectric layer of the plurality of dielectric layers.

BRIEF DESCRIPTION OF THE DRAWINGS

The present disclosure may be understood by reference to the accompanying drawings, when considered in conjunction with the subsequent detailed description, in which.

DETAILED DESCRIPTION

Particular embodiments of the present disclosure will be described below with reference to the accompanying drawings. In the following description, well-known functions or constructions are not described in detail to avoid obscuring the present disclosure in unnecessary detail. Those skilled in the art will understand that embodiments of the present disclosure may be adapted for use with any electrosurgical system, generator, and/or instrument. It should also be appreciated that different electrical and mechanical connections and other considerations may apply to each particular type of instrument.

Briefly, an electrosurgical generator according to the present disclosure may be used in monopolar and/or bipolar electrosurgical procedures, including, for example, cutting, coagulation, ablation, and vessel sealing procedures. The generator may include a plurality of outputs for interfacing with various electrosurgical instruments (e.g., monopolar instruments, return electrode pads, bipolar electrosurgical forceps, footswitches, etc.). Further, the generator may include electronic circuitry configured to generate radio frequency energy specifically suited for powering electrosurgical devices operating in various electrosurgical modes (e.g., cut, blend, coagulate, division with hemostasis, fulgurate, spray, etc.) and procedures (e.g., monopolar, bipolar, vessel sealing).

Figure 1:
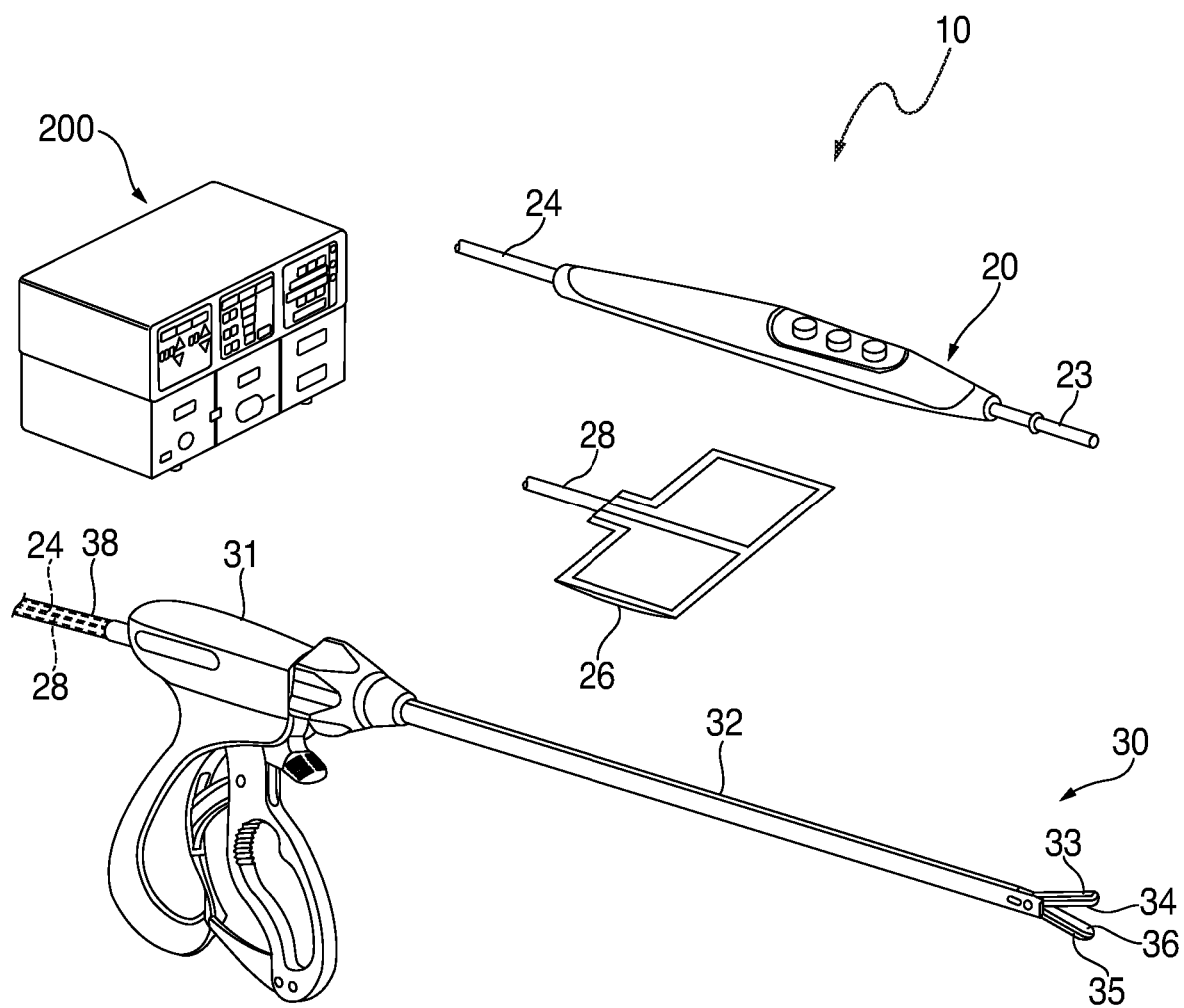
FIG. 1 is a perspective view of an electrosurgical system according to an embodiment of the present disclosure.

Referring to FIG. 1, an electrosurgical system 10 according to the present disclosure includes one or more monopolar electrosurgical instruments 20 having one or more active electrodes 23 (e.g., electrosurgical cutting probe, ablation electrode(s), etc.) for treating tissue of a patient. Electrosurgical alternating RF current is supplied to the instrument 20 by a generator 200 via a supply line 24 that is connected to an active terminal 350 (FIG. 3) of the generator 200, allowing the instrument 20 to cut, coagulate, and/or otherwise treat tissue. The RF current is returned to the generator 200 through a return electrode pad 26 via a return line 28 at a return terminal 352 (FIG. 3) of the generator 200. For monopolar operation, the system 10 may include a plurality of return electrode pads 26 that, in use, are disposed on a patient to minimize the chances of tissue damage by maximizing the overall contact area with the patient. In addition, the generator 200 and the return electrode pads 26 may be configured for monitoring tissue-to-patient contact to ensure that sufficient contact exists therebetween.

Figure 3:
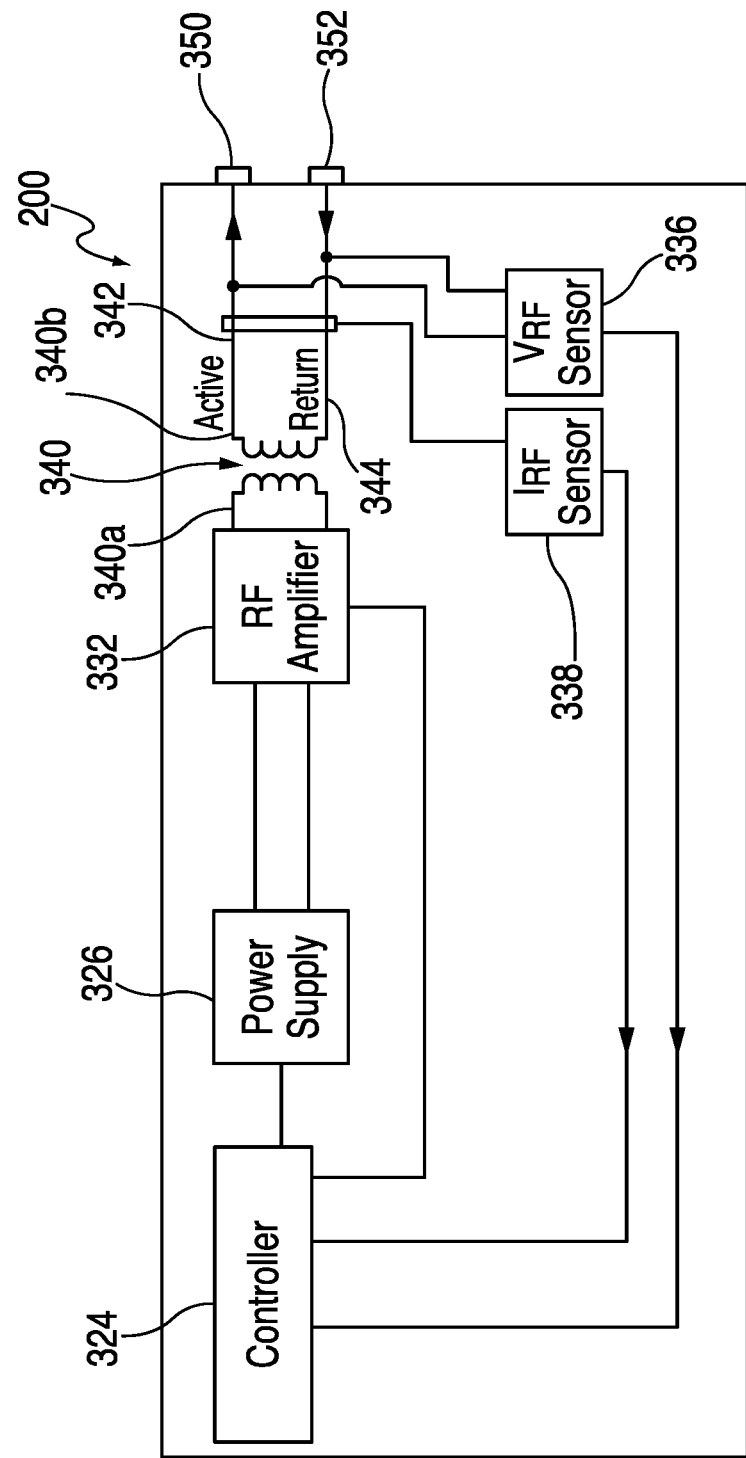
FIG. 3 is a schematic diagram of the electrosurgical generator of FIG. 2.

The system 10 may also include one or more bipolar electrosurgical instruments, for example, a bipolar electrosurgical forceps 30 having one or more electrodes for treating tissue of a patient. The electrosurgical forceps 30 includes a housing 31 and opposing jaw members 33 and 35 disposed at a distal end of a shaft 32. The jaw members 33 and 35 have one or more active electrodes 34 and a return electrode 36 disposed therein, respectively. The active electrode 34 and the return electrode 36 are connected to the generator 200 through cable 38 that includes the supply and return lines 24, 28, which may be coupled to the active and return terminals 350, 352, respectively (FIG. 3). The electrosurgical forceps 30 is coupled to the generator 200 at a port having connections to the active and return terminals 350 and 352 (e.g., pins) via a plug disposed at the end of the cable 38, wherein the plug includes contacts from the supply and return lines 24, 28 as described in more detail below.

Figure 2:
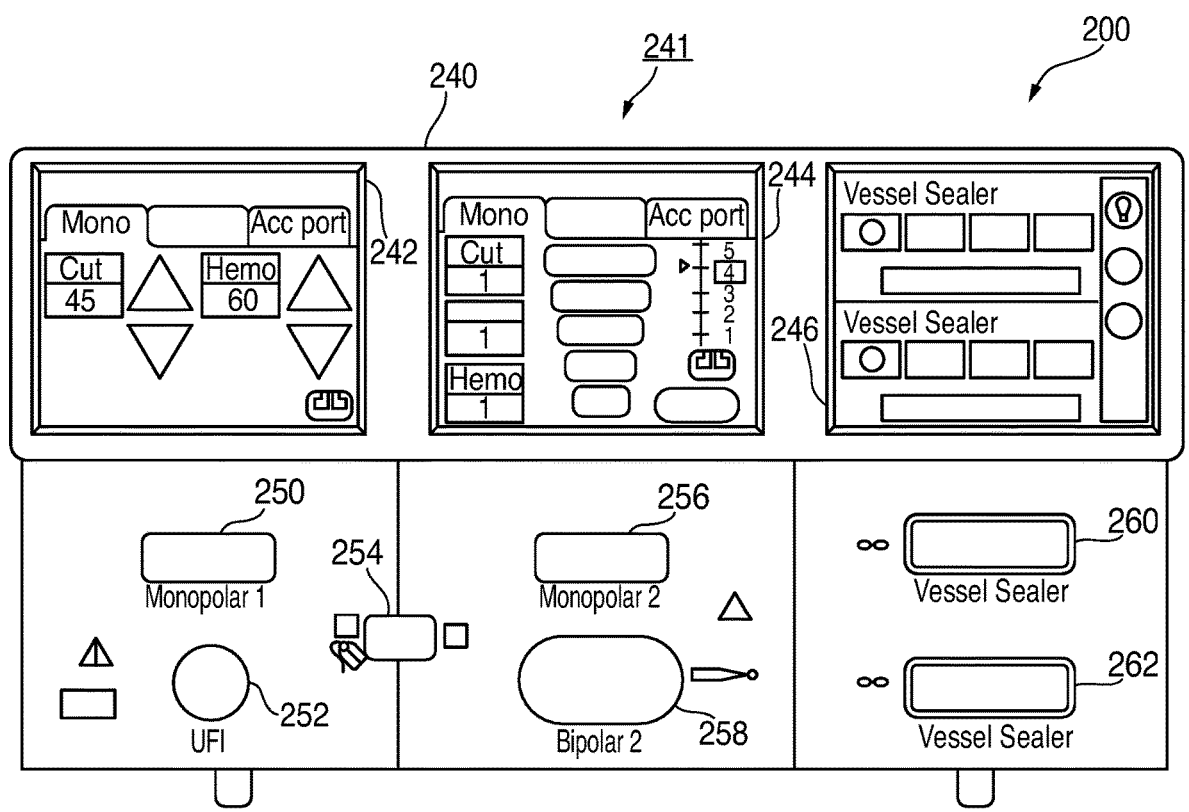
FIG. 2 is a front view of an electrosurgical generator of the electrosurgical system of FIG. 1.

With reference to FIG. 2, a front face 240 of the generator 200 is shown. The generator 200 may include a plurality of ports 250-262 to accommodate various types of electrosurgical instruments (e.g., monopolar electrosurgical instrument 20, electrosurgical forceps 30, etc.).

The generator 200 includes a user interface 241 having one or more display screens 242, 244, 246 for providing the user with variety of output information (e.g., intensity settings, treatment complete indicators, etc.). Each of the screens 242, 244, 246 is associated with a corresponding port 250-262. The generator 200 includes suitable input controls (e.g., buttons, activators, switches, touch screen, etc.) for controlling the generator 200. The screens 242, 244, 246 are also configured as touch screens that display a corresponding menu for the instruments (e.g., electrosurgical forceps 30, etc.). The user may adjust inputs by simply touching corresponding menu options.

Screen 242 controls monopolar output and the devices connected to the ports 250 and 252. Port 250 is configured to couple to a monopolar electrosurgical instrument (e.g., electrosurgical instrument 20) and port 252 is configured to couple to a foot switch (not shown). The foot switch provides for additional inputs (e.g., replicating inputs of the generator 200). The port 254 is configured to couple to the return electrode pad 26. Screen 244 controls monopolar and bipolar output and the devices connected to the ports 256 and 258. Port 256 is configured to couple to other monopolar instruments. Port 258 is configured to couple to a bipolar instrument (not shown).

Screen 246 controls the electrosurgical forceps 30 that may be plugged into one of the ports 260 and 262, respectively. The generator 200 outputs energy through the ports 260 and 262 suitable for sealing tissue grasped by the electrosurgical forceps 30. In particular, screen 246 outputs a user interface that allows the user to input a user-defined intensity setting for each of the ports 260 and 262. The user-defined setting may be any setting that allows the user to adjust one or more energy delivery parameters, such as power, current, voltage, energy, etc. or sealing parameters, such as energy rate limiters, sealing duration, etc. The user-defined setting is transmitted to a controller 324 (FIG. 3) where the setting may be saved in memory. In embodiments, the intensity setting may be a number scale, such as for example, from one to ten or one to five. In embodiments, the intensity setting may be associated with an output curve of the generator 200. The intensity settings may be specific for each electrosurgical forceps 30 being utilized, such that various instruments provide the user with a specific intensity scale corresponding to the electrosurgical forceps 30. The active and return terminals 350 and 352 may be coupled to any of the desired ports 250-262.

With reference to FIG. 3, the generator 200 also includes a controller 324, a power supply 326, and a power converter 332. The power supply 326 may be a high voltage, DC power supply connected to an AC source (e.g., line voltage) and provides high voltage, DC power to the power converter 332, which then converts high voltage, DC power into RF energy and delivers the energy to the active terminal 350. The energy is returned thereto via the return terminal 352. In particular, electrosurgical energy for energizing the monopolar electrosurgical instrument 20 and/or electrosurgical forceps 30 is delivered through the active and return terminals 350 and 352. The active and return terminals 350 and 352 are coupled to the power converter 332 through an isolation transformer 340. More specifically, the isolation transformer 340 includes a primary winding 340a coupled to the power converter 332 and a secondary winding 340b having an active lead 342 coupled to the active terminal 350 and a return lead 344 coupled to the return lead 344. The output of power converter 332 transmits current through the isolation transformer 340 to the load "Z", e.g., tissue being treated.

The power converter 332 is configured to operate in a plurality of modes, during which the generator 200 outputs corresponding waveforms having specific duty cycles, peak voltages, crest factors, etc. It is envisioned that in other embodiments, the generator 200 may be based on other types of suitable power supply topologies. Power converter 332 may be a resonant RF amplifier or a non-resonant RF amplifier. A non-resonant RF amplifier, as used herein, denotes an amplifier lacking any tuning components, e.g., conductors, capacitors, etc., disposed between the power converter and the load "Z."

The controller 324 includes a processor (not shown) operably connected to a memory (not shown), which may include one or more of volatile, non-volatile, magnetic, optical, or electrical media, such as read-only memory (ROM), random access memory (RAM), electrically-erasable programmable ROM (EEPROM), non-volatile RAM (NVRAM), or flash memory. The processor may be any suitable processor (e.g., control circuit) adapted to perform the operations, calculations, and/or set of instructions described in the present disclosure including, but not limited to, a hardware processor, a field programmable gate array (FPGA), a digital signal processor (DSP), a central processing unit (CPU), a microprocessor, and combinations thereof. Those skilled in the art will appreciate that the processor may be substituted for by using any logic processor (e.g., control circuit) adapted to perform the calculations and/or set of instructions described herein.

The controller 324 includes output ports that are operably connected to the power supply 326 and/or the power converter 332 allowing the controller 324 to control the output of the generator 200 according to either open and/or closed control loop schemes. A closed loop control scheme is a feedback control loop, in which a plurality of sensors measure a variety of tissue and energy properties (e.g., tissue impedance, tissue temperature, output power, current and/or voltage, etc.), and provide feedback to the controller 324. The controller 324 then controls the power supply 326 and/or the power converter 332, which adjusts power delivered to and/or from the power converter 332, respectively. The controller 324 also receives input signals from the input controls of the generator 200, the instrument 20, and/or electrosurgical forceps 30. The controller 324 utilizes the input signals to adjust power outputted by the generator 200 and/or performs other control functions thereon.

The controller 324 may perform various mathematical computations in order to control the power supply 326 and/or the power converter 332 to generate an RF waveform having a desired shape and energy content. Examples of computations performed by the controller 324 include, but are not limited to, calculating instantaneous and/or root mean square power levels, amount of energy delivered on a cycle by cycle basis, load impedance, etc.

The generator 200 according to the present disclosure may also include a plurality of sensors, namely, a voltage sensor 336 and a current sensor 338. The voltage sensor 336 is coupled to the active and return leads 342, 344 and measure RF voltage supplied to the active and return terminals 350, 352. The current sensor 338 is coupled to the active and/or return leads 342, 344 and measures RF current supplied to the active and return terminals 350, 352. In embodiments, the generator 200 may also include additional sensors (not shown) coupled to the power supply 326.

Figure 4:
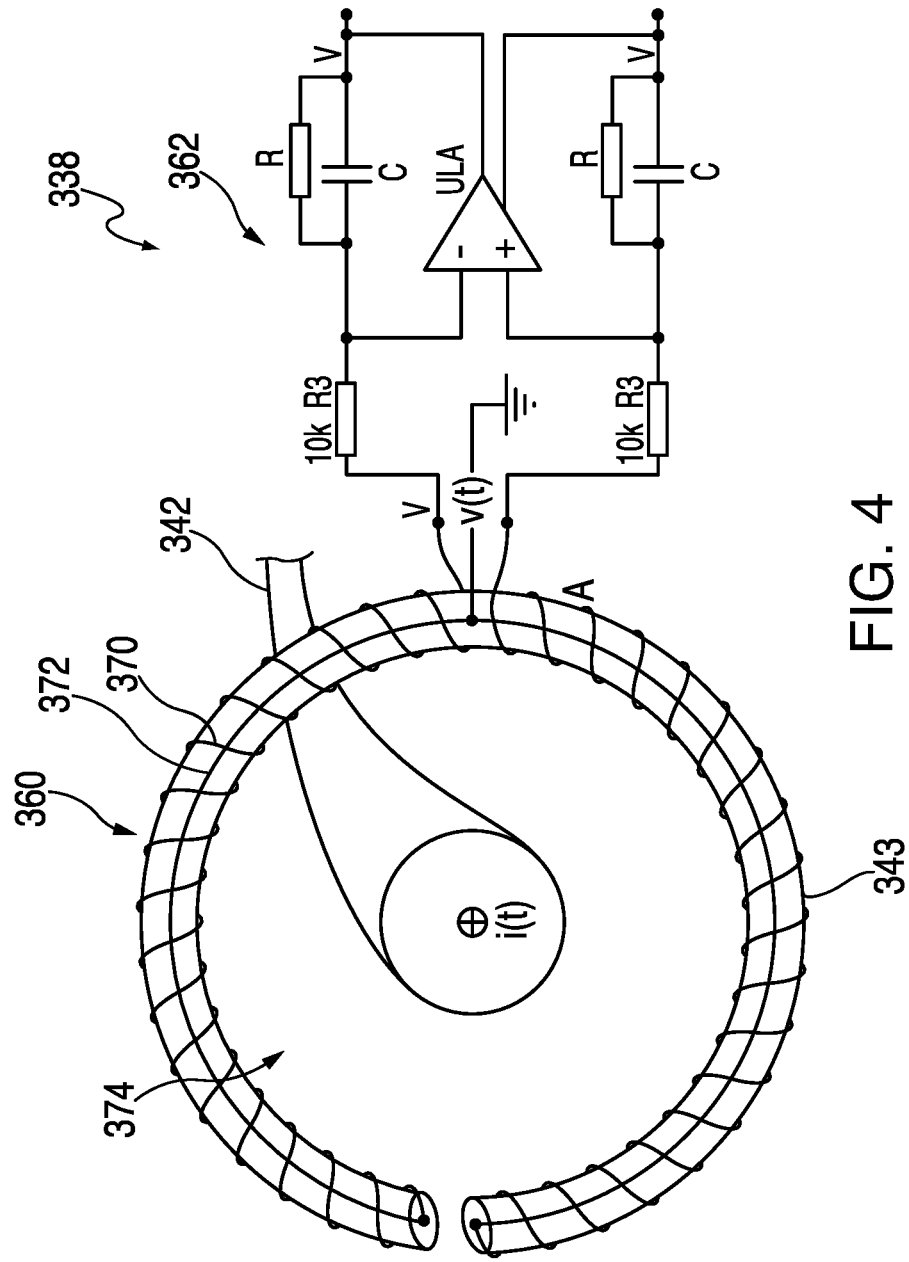
FIG. 4 is a schematic diagram of a current sensor of the electrosurgical generator of FIG. 2.

With reference to FIG. 4, the current sensor 338 includes a current sense coil 360 and a conditioning circuit 362. The conditioning circuit 362 processes (e.g., integrates) the signal from the current sense coil 360, which is a time-derivative of the current being measured passing through the active lead 342. The current sense coil 360 includes an outer coil 370 (e.g., a toroid) that acts as an active conductor wrapped around an inner conductor 372 (e.g., a "Bucking coil") that acts as a return conductor. The current sense coil 360 defines an opening 374, through which the current lead 342 is passed through. This configuration allows for the outer coil 370 and the inner conductor 372 to measure current passing through the active lead 342 based on the magnetic fields generated by the current. In particular, the outer coil 370 detects a first magnetic field generated by the current passing through the active lead 342 and produces a first voltage corresponding thereto. The outer coil 370 may also detect a second magnetic field, which produces a second voltage. The second magnetic field is orthogonal to the first magnetic field and is not related to the sensed current, and thus, its effects on the outer coil 370 is removed to achieve accurate current measurement. The inner conductor 372 senses the second magnetic field and produces a third voltage proportional to the second magnetic field. The second voltage and third voltage have approximately the same magnitude such that they cancel each other, which allows for the conditioning circuit 362 to determine the first voltage corresponding to the current passing through the active lead 342. In embodiments, the current sense coil 360 may be implemented on a printed circuit board. In further embodiments, the current sense coil 360 may also be implemented by winding a wire around a core 343, which may be a toroidal magnetic core or a low permeability core.

Figure 5:
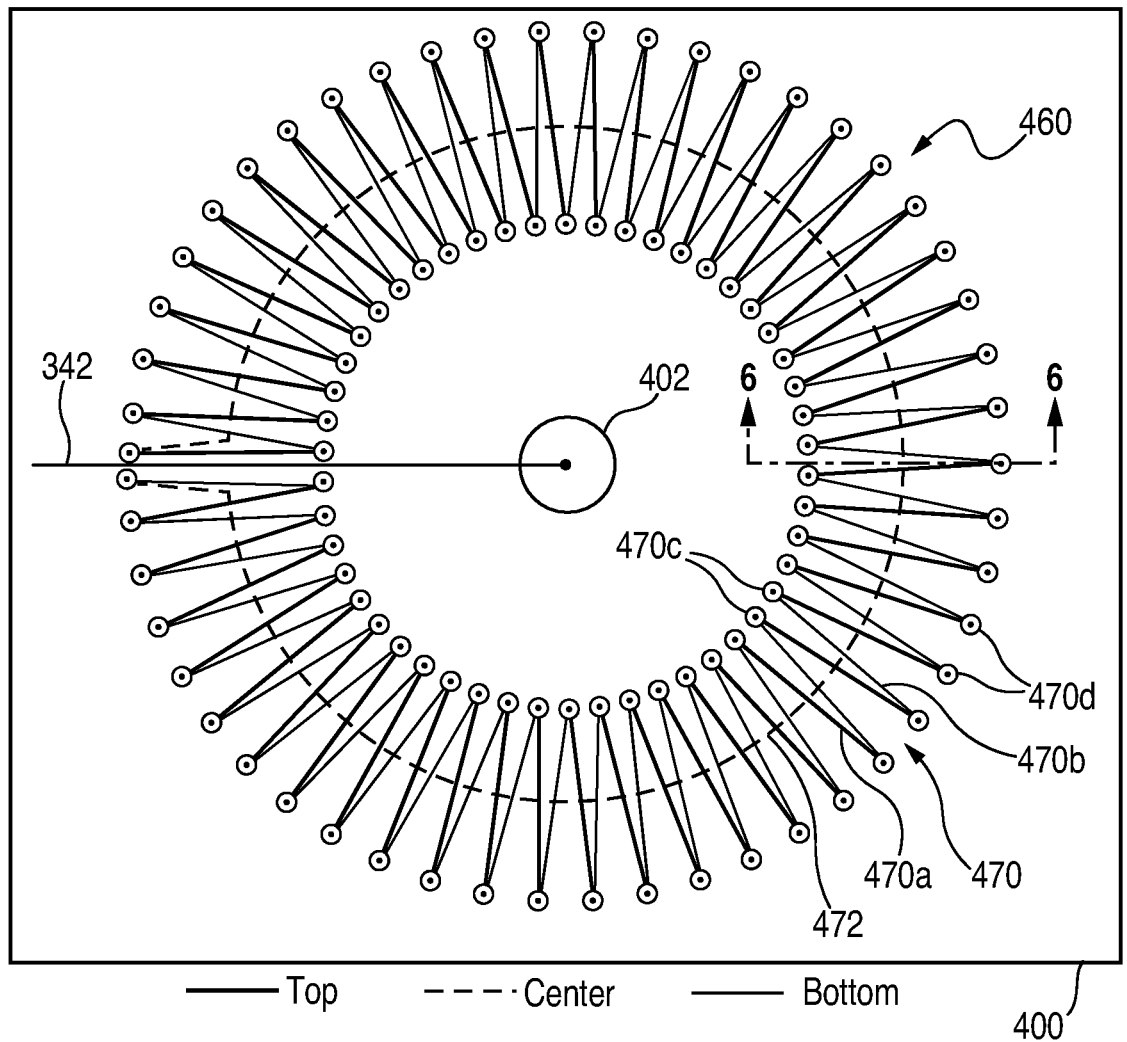
FIG. 5 is a schematic diagram of a current sense coil of the current sensor of FIG. 4 disposed on a printed circuit board.
Figure 6:
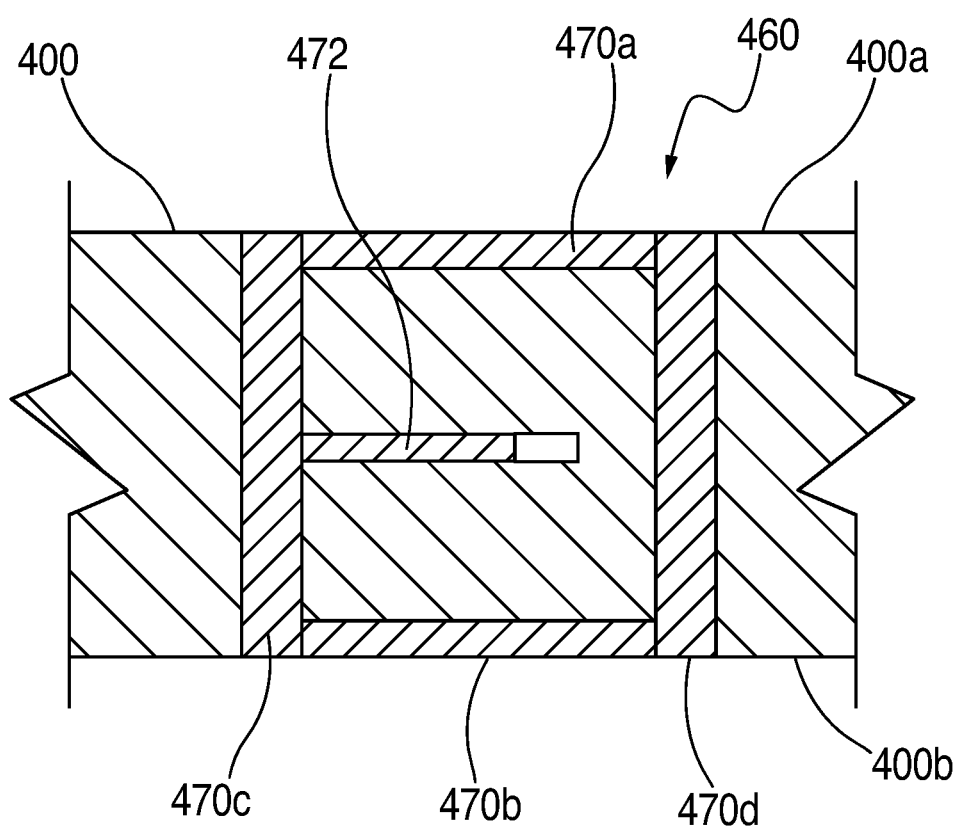
FIG. 6 is a cross-sectional side view taken along a sectional line 6-6 of the current sense coil of FIG. 5.

With reference to FIGS. 5 and 6, a current sense coil 460 is disposed on a printed circuit board ("PCB") 400. The current sense coil 460 is substantially similar to the current sense coil 360 and only the differences therebetween are described below to avoid unnecessary repetition. The PCB 400 may be a multilayer PCB formed from any suitable dielectric material, including, but not limited to composite materials composed of woven fiberglass cloth with an epoxy resin binder such as FR-4 grade as designated by National Electrical Manufacturers Association. The PCB 400 defines an opening 402 therethrough for passage of the active lead 342. The current sense coil 460 includes an outer coil 470 and an inner conductor 472. The outer coil 470 is formed by a plurality of upper conductive traces 470a and lower conductive traces 470b interconnected by a plurality of inner conductive vias 470c and outer conductive vias 470d. The upper and lower conductive traces 470a and 470b may be printed on respective upper and lower surfaces 400a, 400b of the PCB 400. The inner conductor 472 is disposed in between the upper and lower conductive traces 470a and 470b and is embedded within the PCB 400 (FIG. 6).

Figure 8:
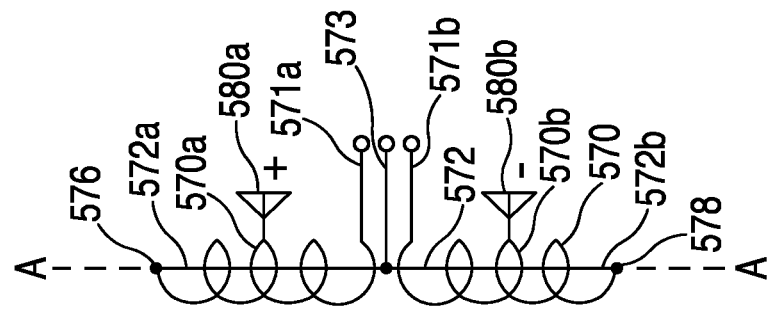
FIG. 8 is a side schematic view of the current sense coil of FIG. 7.
Figure 7:
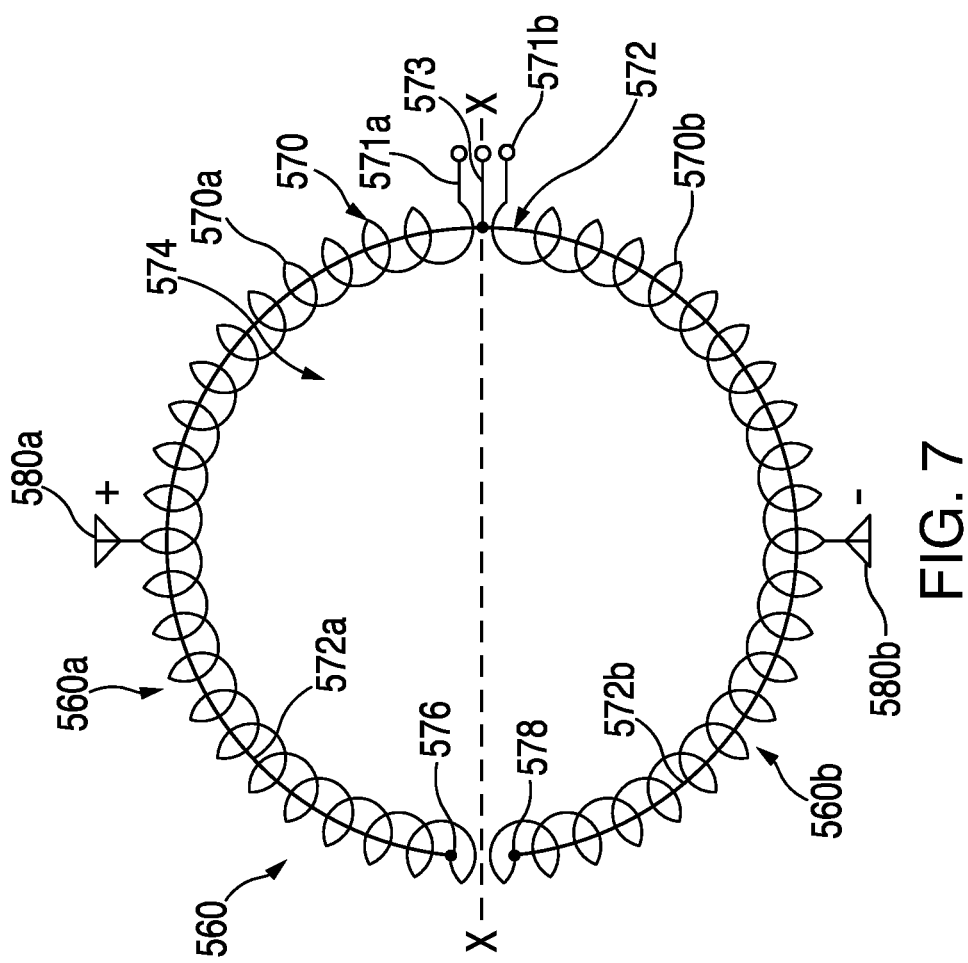
FIG. 7 is a top schematic view of a current sense coil according to another embodiment of the present disclosure.

With reference to FIGS. 7 and 8, a current sense coil 560, which is substantially similar to the current sense coil 360, includes two balancing portions 560a and 560b, which are symmetrical about an axis "X-X" (FIG. 7). The current sense coil 560 is also configured to couple to the sense circuit 362 (FIG. 4). The current sense coil 560 includes an outer coil 570 (e.g., toroid) that acts as an active conductor wrapped around an inner conductor 572. The current sense coil 560 defines an opening 574, through which the current lead 342 (FIG. 4) is passed through. The outer coil 570 includes two balancing portions 570a and 570b, each of which is coupled to a conditioning circuit (e.g., conditioning circuit 362) by a lead 571a and 571b, respectively. The inner conductor 572 also includes two balancing portions 572a and 572b, both of which are coupled to the conditioning circuit 362 by a center-tapped lead 573. Balancing portion 570a of the outer coil 570 is coupled to the balancing portion 572a of the inner conductor 572 at a node 576 and the balancing portion 570b of the outer coil 570 is coupled to the balancing portion 572b of the inner conductor 572 at a node 578. Thus, the balancing portions 570a and 572a along with counterpart balancing portions 570b and 572b form the balancing portions 560a and 560b of the current sense coil 560.

Although, this configuration illustrated in FIGS. 7 and 8 provides for cancellation of some unwanted external electric fields, it may result in other interference. In particular, the current sense coil 560 acts as an inductively loaded, center-tapped dipole antenna with the balancing portions 560a and 560b acting as two poles. As such, any near-field alternating current with a differential component in a plane "A-A" (FIG. 8) defined by the current sense coil 560, induces a differential voltage (and therefore current) in the outer coil 570 as represented by electrical fields 580a and 580b.

Figure 9:
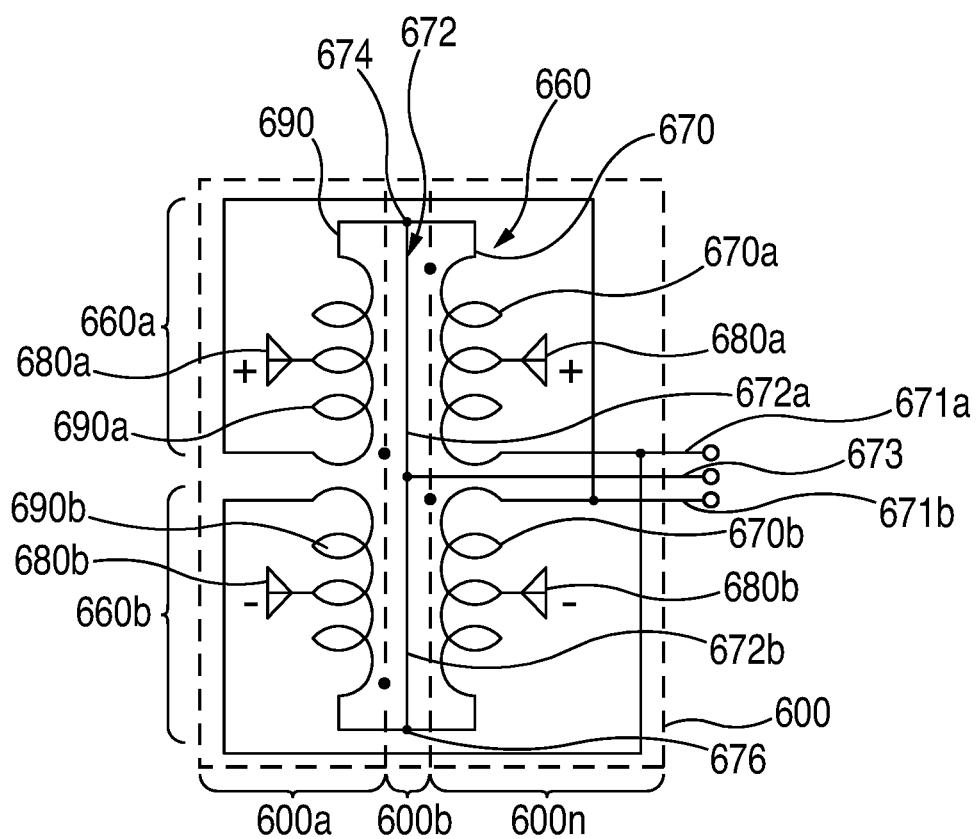
FIG. 9 is a side schematic view of a current sense coil according to a further embodiment of the present disclosure.

With reference to FIG. 9, a current sense coil 660, which is configured to cancel out the induced electrical fields, includes a first outer coil 670, a second outer coil 690, and an inner conductor 672 disposed therebetween. The current sense coil 660 is also configured to couple to the sense circuit 362 (FIG. 4). Similar to the current sense coil 560 of FIGS. 7 and 8, the current sense coil 660 also includes two balancing portions 660a and 660b. In particular, the first outer coil 670 includes a first balancing portion 670a, and a second balancing portion 670b. The second outer coil 690 includes a first balancing portion 690a and a second balancing portion 690b. The inner conductor 672 includes a first balancing portion 672a and a second balancing portion 672b. The first and second balancing portions 672a and 672b are coupled to the conditioning circuit 362 (FIG. 4) by a center-tapped lead 673.

The first outer coil 670 and the second outer coil 690 have the same shape, namely, arcuate, and define a surface area sufficient to insure that they are affected by external electric fields in the same manner and thus pick up the same amount of interference. Each of the first and second outer coils 670 and 690 are configured to detect the first magnetic field generated by the current passing through the active lead 342.

With continued reference to FIG. 9, the first balancing portion 670a of the first outer coil 670 and the second balancing portion 690b of the second outer coil 690 are coupled to a first lead 671a, whereas the second balancing portion 670b of the first outer coil 670 and the first balancing portion 690a of the second outer coil 690 are coupled to a second lead 671b. In addition, the first balancing portions 670a and 690a of the first and second outer coils 670 and 690, respectively, are coupled to the first balancing portion 672a of the inner conductor 672 at a first node 674. The second balancing portions 670b and 690b of the first and second outer coils 670 and 690, respectively, are coupled to the second balancing portion 672b of the inner conductor 672 at a second node 676. The first and second balancing portions 690a and 690b of the second outer coil 690 are also wound in an opposite direction from that of the first and second balancing portions 670a and 670b of the first outer coil 670. The inverse configuration of the first and second outer coils 670 and 690, namely, opposing pairs of the first balancing portions 670a and 690a and second balancing portions 690a and 690b being wound in opposite direction and coupled together at first and second leads 671a and 671b, respectively, cancels out induced electrical fields 680a and 680b since the voltage corresponding to each of the fields 680a and 680b is supplied to each of the leads 671a and 671b.

Figure 10:
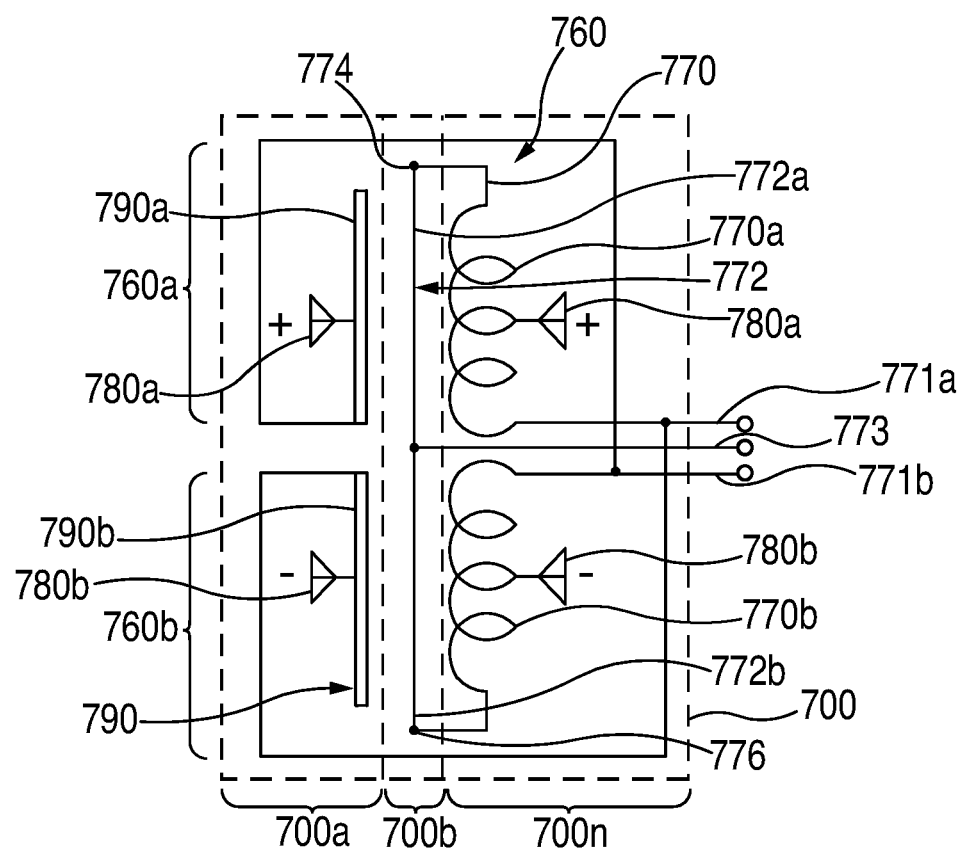
FIG. 10 is a side schematic view of a current sense coil according to yet another embodiment of the present disclosure.

With reference to FIG. 10 a current sense coil 760, which is also configured to cancel out the induced electrical fields, includes an outer coil 770, a conductive plane 790, and an inner conductor 772 disposed therebetween. The current sense coil 760 is also configured to couple to the sense circuit 362 (FIG. 4). Similar to the current sense coil 660 of FIG. 9, the current sense coil 760 also includes two balancing portions 760a and 760b. In particular, the outer coil 770 includes a first balancing portion 770a, and a second balancing portion 770b. The conductive plane 790 includes a first balancing portion 790a and a second balancing portion 790b. The inner conductor 772 includes a first balancing portion 772a and a second balancing portion 772b. The first and second balancing portions 772a and 772b are coupled to the conditioning circuit 362 by a center-tapped lead 773.

The conductive plane 790 has a hemispherical shape and defines a surface area which covers the circular shape and area defined by the outer coil 770, which is similar to the shape and surface area of the outer coil 560 of FIG. 7. This ensures that the conductive plane 790 is affected by external electric fields in the same manner as the outer coil 770, and thus, picks up the same amount of interference to cancel out the induced electrical fields. The first balancing portion 770a of the first outer coil 770 and the second balancing portion 790b of the conductive plane 790 are coupled to a first lead 771a, whereas the second balancing portion 770b of the first outer coil 770 and the first balancing portion 790a of the conductive plane 790 are coupled to a second lead 771b. In addition, the first balancing portion 770a of the outer coil 770 is coupled to the first balancing portion 772a of the inner conductor 772 at a first node 774. The second balancing portion 770b of the outer coil 770 is coupled to the second balancing portion 772b of the inner conductor 772 at a second node 776. The inverse connection of the outer coil 770 and the conductive plane 790, namely, opposing pairs of the first balancing portions 770a and 790a and second balancing portions 770b and 790b being coupled together at first and second leads 771a and 771b, respectively, cancels out the induced electrical fields 780a and 780b since the voltage corresponding to each of the fields 780a and 780b is supplied to each of the leads 771a and 771b.

Each of the current sense coils 670 and 770 of FIGS. 9 and 10, respectively, are coupled to the conditioning circuit 362 (FIG. 4), which processes the voltage signals passed thereto. The current sense coils 670 and 770 of FIGS. 9 and 10 may also be implemented within a multilayer PCB, namely, PCB 600 and PCB 700, respectively. With reference to FIGS. 9 and 10, each of the components of the current sense coil 660 (i.e., the first outer coil 670, the second outer coil 690, and the inner conductor 672) and counterpart components of the current sense coil 760 (i.e., the outer coil 770, the conductive plane 790, and the inner conductor 772) may be disposed across multiple layers of the PCB 600 and PCB 700, respectively, in a manner described above with respect to the current sense coil 460 and PCB 400. In particular, each of the components of the current sense coils 660 and/or 760 maybe formed by forming conductive traces on individual layers 600a, 600b, ... 600n of the PCB 600 and layers 700a, 700b, ... 700n of the PCB 700, respectively. In addition, the components of the current sense coils 660 and/or 760 may be interconnected across multiple layers by conductive vias, which pass through the dielectric layers of the PCB 600 and PCB 700.

While several embodiments of the disclosure have been shown in the drawings and/or described herein, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope of the claims appended hereto.

What is claimed is:

1. A current sensor comprising:
   a current sense coil disposed about a conductive lead, the current sense coil configured to sense a current passing through the conductive lead, the current sense coil including:
   a first outer coil configured to detect a first magnetic field, the first outer coil including:
   a first balancing portion forming a first half of a circumference of the first outer coil, wherein an entirety of the first half of the circumference of the first outer coil is wound in a first direction; and
   a second balancing portion forming a second half of the circumference of the first outer coil and wound in a second direction, opposite the first direction;
   a second outer coil configured to detect the first magnetic field, the second outer coil including:
   a third balancing portion forming a first half of a circumference of the second outer coil and wound in a third direction, opposite the first direction; and
   a fourth balancing portion forming a second half of the circumference of the second outer coil and wound in a fourth direction, opposite the second direction and the third direction; and
   an inner conductor disposed between the first outer coil and the second outer coil, the inner conductor configured to detect a second magnetic field generated by the current.

2. The current sensor according to claim 1, wherein the first balancing portion of the first outer coil and the second balancing portion of the second outer coil are coupled to a first lead.

3. The current sensor according to claim 2, wherein the second balancing portion of the first outer coil and the first balancing portion of the second outer coil is coupled to a second lead.

4. The current sensor according to claim 3, further comprising a conditioning circuit coupled to the first lead and the second lead.

5. The current sensor according to claim 1, wherein each of the first outer coil and the second outer coil are coupled to the inner conductor.

6. The current sensor according to claim 1, further comprising a printed circuit board having a plurality of dielectric layers.

7. The current sensor according to claim 6, wherein each of the first outer coil, the second outer coil, and the inner conductor is disposed on a corresponding dielectric layer of the plurality of dielectric layers.

8. An electrosurgical generator comprising:
   a power supply configured to output a direct current;
   a power converter coupled to the power supply, the power converter configured to generate a radio frequency current based on the direct current;
   at least one lead coupling the power converter to a terminal configured to couple to an electrosurgical instrument; and
   a current sensor including:
   a current sense coil disposed about the at least one lead, the current sense coil configured to sense the radio frequency current passing through the at least one lead, the current sense coil including:
   a first outer coil configured to detect a first magnetic field, the first outer coil including:
   a first balancing portion forming a first half of a circumference of the first outer coil, wherein an entirety of the first half of the circumference of the first outer coil is wound in a first direction; and
   a second balancing portion forming a second half of the circumference of the first outer coil and wound in a second direction, opposite the first direction;
   a second outer coil configured to detect the first magnetic field, the first outer coil including:
   a third balancing portion forming a first half of a circumference of the second outer coil and wound in a third direction, opposite the first direction; and
   a fourth balancing portion forming a second half of the circumference of the second outer coil and wound in a fourth direction, opposite the second direction and the third direction; and
   an inner conductor disposed between the first outer coil and the second outer coil, the inner conductor configured to detect a second magnetic field generated by the radio frequency current.

9. The electrosurgical generator according to claim 8, wherein the first balancing portion of the first outer coil and the second balancing portion of the second outer coil are coupled to a first lead.

10. The electrosurgical generator according to claim 9, wherein the second balancing portion of the first outer coil and the first balancing portion of the second outer coil are coupled to a second lead.

11. The electrosurgical generator according to claim 10, wherein the current sensor further includes a conditioning circuit coupled to the first lead and the second lead.

12. The electrosurgical generator according to claim 8, wherein each of the first outer coil and the second outer coil is coupled to the inner conductor.

13. The electrosurgical generator according to claim 8, wherein the current sensor further includes a printed circuit board having a plurality of dielectric layers.

14. The electrosurgical generator according to claim 13, wherein each of the first outer coil, the second outer coil, and the inner conductor is disposed on a corresponding dielectric layer of the plurality of dielectric layers.

* * * * *